US009790158B2

(12) United States Patent
Wright et al.

(10) Patent No.: US 9,790,158 B2
(45) Date of Patent: Oct. 17, 2017

(54) SUBSTITUTED TROPOLONE DERIVATIVES AND METHODS OF USE

(71) Applicant: University of Connecticut, Farmington, CT (US)

(72) Inventors: Dennis L. Wright, Storrs, CT (US); Amy C. Anderson, Storrs, CT (US); Michael Van Heyst, Glastonbury, CT (US); Sophia Ononye, New Britain, CT (US)

(73) Assignee: UNIVERSITY OF CONNECTICUT, Farmington, CT (US)

( * ) Notice: Subject to any disclaimer, the term of this patent is extended or adjusted under 35 U.S.C. 154(b) by 24 days.

(21) Appl. No.: 14/409,276

(22) PCT Filed: Jun. 21, 2013

(86) PCT No.: PCT/US2013/047118
§ 371 (c)(1),
(2) Date: Dec. 18, 2014

(87) PCT Pub. No.: WO2013/192554
PCT Pub. Date: Dec. 27, 2013

(65) Prior Publication Data
US 2015/0166448 A1    Jun. 18, 2015

Related U.S. Application Data

(60) Provisional application No. 61/663,064, filed on Jun. 22, 2012.

(51) Int. Cl.
| C07C 49/717 | (2006.01) |
| C07C 49/747 | (2006.01) |
| C07C 49/753 | (2006.01) |
| A61K 31/122 | (2006.01) |
| C07C 225/20 | (2006.01) |

(52) U.S. Cl.
CPC .......... *C07C 49/717* (2013.01); *C07C 49/747* (2013.01); *C07C 49/753* (2013.01); *C07C 225/20* (2013.01); *C07C 2601/18* (2017.05)

(58) Field of Classification Search
None
See application file for complete search history.

(56) References Cited

U.S. PATENT DOCUMENTS

| 4,057,556 A | 11/1977 | Bagli et al. |
| 4,125,625 A | 11/1978 | Bagli et al. |
| 4,152,457 A | 5/1979 | Bagli et al. |
| 4,183,955 A | 1/1980 | Bagli et al. |

FOREIGN PATENT DOCUMENTS

| EP | 0267378 A2 | 5/1988 |
| EP | 1504759 A1 | 2/2005 |
| JP | 59134720 | 9/1984 |
| JP | 61215341 | 9/1986 |
| JP | 63159343 | 10/1988 |
| JP | 2003073266 | 3/2003 |
| JP | 2004238291 | 8/2004 |
| JP | 2005537294 | 12/2005 |

OTHER PUBLICATIONS

Doering, W.v.E., et al., JACS, 75:2387 (1953).*
Pankratov, A.N., J. Serb. Chem. Soc., 65:1 (2000).*
Cavazza, et al., J.C.S., Chem. Comm., 13:501 (1974).*
Nozoe, et al., Bulletin of the Chemical Society of Japan, 42:3277 (1969).*
Nozoe, et al., Proceedings of the Japan Academy, 8:413 (1952).*
Extended European Search Report, European Patent Application No. 13807181.6 , mailed Oct. 29, 2015, 16 pages.
Akroyd et al., "755. Purpurogallin. Part IX. The Structure of the Isomeric O-Methyl Ethers of β-methyltropolone", Journal of the Chemical Society, Jan. 1951, p. 3427.
Asao et al., "Novel Rearrangement of the Adduct of 6,6-Dimethylfulvene and Dichloroketen", Journal of the Chemical Society D: Chemical Communications, No. 2, Jan. 1970, p. 89.
Dokmanovic et al., "Histone Deacetylase Inhibitors: Overview and Perspectives", Molecular Cancer Research, American Association for Cancer Research, vol. 5, No. 10, Oct. 2007, pp. 981-989.
Kitahara et al., "The Synthesis of Nootkatin. a Sesquiterpenoid Tropolone", Bulletin of the Chemical Society, vol. 31, No. 6, Jan. 1958, pp. 782-783.
Koufaki et al., "Synthesis of Tropolone Derivatives and Evaluation of Their in Vitro Neuroprotective Activity", European Journal of Medicinal Chemistry, Editions Scientifique Elsevier, vol. 45, No. 3, Mar. 2010, pp. 1107-1112.
Lee et al., "Stereo- and Regiocontrolled Hydroxylation of Oxyallyl [4+3] Cycloadducts. A Concise Synthesis of Hinokitiol", Tetrahedron Letters, Pergamon, vol. 40, No. 43, Oct. 1999, pp. 7675-7678.
Li et al., "Optimization of Potent Hepatitis C Virus NS3 Helicase Inhibitors Isolated from the Yellow Dyes Thioflavine S and Primuline", Journal of Medicinal Chemistry, vol. 55, No. 7, Apr. 12, 2012, pp. 3319-3330.
Liu et al., "Hinokitiol, a Metal Chelator Derived from Natural Plants, Suppresses Cell Growth and Disrupts Androgen Receptor Signaling in Prostate Carcinoma Cell Lines", Biochemical and Biophysical Research Communications, Academic Press Inc, vol. 351, No. 1, Dec. 8, 2006, pp. 26-32.
Liu et al., "p27-Associated G1 Arrest Induced by Hinokitiol in Human Malignant Melanoma Cells is Mediated via Down-Regulation of pRb, Skp2 Ubiquitin Ligase, and Impairment of Cdk2 Function", Cancer Letters, vol. 286, No. 2, Dec. 2009, pp. 240-249.
Mukai , "Reaction of 2-Chloro-3-phenyltropone and 2-Chloro-7-phenyltropone with Ammonia and Amines", Bulletin of the Chemical Society of Japan, vol. 32, No. 3., Jan. 1959, pp. 272-279.

(Continued)

*Primary Examiner* — Michael Barker
(74) *Attorney, Agent, or Firm* — Kilpatrick Townsend & Stockton LLP

(57) ABSTRACT

The compositions and methods described herein relate generally to substituted tropolone derivatives, which, among other features, are useful as histone deacetylase (HDAC) inhibitors.

28 Claims, No Drawings

(56) References Cited

OTHER PUBLICATIONS

Muroi et al., "Mercapto Derivatives of 2-Phenyltropone and 2-(p-Meth oxyphenyl)-Tropone", Nippon Kagaku Zassi, vol. 80, No. 2, Jan. 1959, pp. 185-188.

Noyori et al., "Natural Product Synthesis via the Polybromo Ketone-Iron Carbonyl Reaction", Tetrahedron, vol. 41, No. 24, Jan. 1985, pp. 5879-5886.

International Preliminary Report on Patentability, PCT Application No. PCT/US2013/047118, mailed Dec. 31, 2014, 6 pages.

Piettre et al., "Monoaryl- and Bisaryldihydroxytropolones as Potent Inhibitors of Inositol Monophosphatase.", Journal of Medicinal Chemistry, vol. 40, No. 26, Dec. 19, 1997, pp. 4208-4221.

Seidel et al., "Histone Deacetylase Modulators Provided by Mother Nature", Genes & Nutrition ; Studying the Relationship Between Genetics and Nutrition in the Improvement of Human Health, vol. 7, No. 3, Feb. 12, 2012, pp. 357-367.

Sunagawa et al., "Studies on Seven-Membered Ring Compounds. XXV. Chlorination of Cycloheptimidazol-2 (1H)-One Derivatives", Chemical & Pharmaceutical Bulletin, vol. 16, No. 7, Jan. 1968, pp. 1300-1307.

Takahashi , "The Tropylation of Polyhydric Phenols and the Dehydrogenation of Their Products", Bulletin of the Chemical Society, vol. 40, No. 6, Jan. 1967, pp. 1462-1473.

Najda-Bernatowicz et al., Studies on the Anti-Hepatitits C Virus Activity of Newly Synthesized Tropolone Derivatives: Identification of NS3 Helicase Inhibitors that Specifically Inhibit Subgenomic HCV Replication, Bioorganic & Medicinal Chemistry, vol. 18, 2010, pp. 5129-5136.

International Search Report and Written Opinion, PCT Application No. PCT/US2013/47118, mailed Nov. 22, 2013.

Japanese Application No. 2015-518615 , "Office Action", Nov. 29, 2016, 7 pages.

Kikuchi , "3-Naphthyltropolones", Nippon Kagaku Zasshi, vol. 10, No. 57, pp. 1439-1442, 2011.

Najda-Bernatowicz et al., "Studies on the anti-hepayis C virus activit y of newly synthesized tropolone derivatives: Identification of NS3 heli case inhibitor that specifically inhibit subgenomic HCV replication", Bioorganic & Medicinal Chemistry, vol. 18, No. 14, Jul. 15, 2010, pp. 5129-5136.

Seto et al., "The Reaction of Tropoids and Quinone Derivatives. II. Reaction of Several Tropolones and p-Benzoquinone", Bulletin of the Chemical Society of Japan, vol. 35, No. 2, 1962.

Shicheng et al., "p27-Associated G1 arrest induced by hinokitiol in human malignant melanoma cells is mediated via down-regulation of pRb, Skp2 ubiquitin ligase, and impairment of Cdk2 function", Cancer Letters, vol. 286, No. 2, Dec. 28, 2009, pp. 240-249.

\* cited by examiner

SUBSTITUTED TROPOLONE DERIVATIVES AND METHODS OF USE

STATEMENT AS TO RIGHTS TO INVENTIONS MADE UNDER FEDERALLY SPONSORED RESEARCH AND DEVELOPMENT

This invention was made with government support under the National Institutes of Health Grant CA162470. The government has certain rights in this invention.

FIELD OF THE INVENTION

The present invention relates generally to substituted tropolone derivatives, which, among other features, are useful as histone deacetylase (HDAC) inhibitors.

DESCRIPTION OF RELATED ART

Malignancies of the digestive organs, collectively, are associated with high rates of morbidity and represent a significant burden to patients and families. Specifically, stomach, colorectal and renal cancers account for 217,000 new cases and 82,000 deaths each year. Surgical treatment for these cancers remains the mainstay and therapeutic treatment options remain limited with few advances in modern medicine.

Modification of chromatin structure by acetylation, phosphorylation and methylation influences gene expression. Histone deacetylase (HDAC) enzymes that tightly control the acetylation status of key lysine residues in the N-termini of histones are key players in cellular processes such as transcription, repair, recombination and replication. As such, HDAC inhibitors have emerged as an attractive antineoplastic therapeutic strategy. The exact mechanism of action is unknown but may be related to induction of apoptosis, cell cycle arrest or inhibition of DNA repair. In October 2006, the FDA approved suberoylanilide hydroxamic acid (SAHA) for cutaneous T-cell lymphomas, but this represents only a small part of the effort to identify HDAC inhibitors for all tumor types, both solid and hematological.

The HDACs are a family of enzymes that belong to four classes that differ in structure and function. Class I (HDAC-1, -2, -3 and -8), IIa (HDAC-4, -5, -7, -9), IIb (HDAC-6 and -10) and IV (HDAC-11) enzymes are zinc-dependent. Class III enzymes are structurally distinct. There are 12 HDAC inhibitors either marketed or in clinical trials for solid and hematological tumors: seven of these are hydroxamic acids, such as vorinostat. All of the inhibitors that have reached an advanced stage include a substituted zinc-chelating group to increase potency. In fact, the use of metal-chelating pharmacophores in drugs to target metalloenzymes has proved to be a successful strategy. Examples include raltegravir that targets two $Mg^{2+}$ ions in HIV integrase, fosmidomycin that targets a zinc ion in IspC and captopril that targets a zinc ion in ACE.

The compounds in clinical trials can be considered to be pan-HDAC inhibitors and exhibit some associated toxicity that may be related to the inhibition of the many functions of the HDAC isoenzymes. An attractive approach is the design of inhibitors for specific classes or even isozymes of HDAC enzymes in order to improve therapeutic effect and reduce toxicity. Class I isozymes (HDAC-1,-2,-3 and -8) are often overexpressed in tumors and correlate with poor prognosis. Specifically, HDAC-8 is overexpressed in pediatric neuroblastoma tumors and HDAC-2 is overexpressed in colon cancers. In contrast, class II (HDAC-4,-5,-6,-7,-9,-10) expression has been correlated with better prognosis. Experiments with mice knockouts of HDAC-3, -5 and -9 show severe adverse cardiac effects, suggesting that inhibitors should not target these enzymes. Overall, it appears that the design of class I inhibitors, especially those that target HDAC-1, -2 and -8, may be an attractive strategy.

BRIEF SUMMARY

The tropolone derivatives, characterized, among other features, by a seven-membered ring and an α-hydroxy ketone, derive from a natural product, β-thujaplicin. Beta-thujaplicin is the principal component of Hiba oil, an extract of cupressaceous trees valued for various antiproliferative properties. Tropolones have also been shown to bind metal ions using the α-hydroxy ketone functionality and to inhibit metalloenzymes. HDAC inhibitors containing a tropolone scaffold would be uniquely capable of providing both potency and selectivity. The lead-like nature of the simple tropolone scaffold affords zinc metal binding, a lipophilic seven-membered ring to interact with the hydrophobic pocket surrounding the zinc ion and three unique positions (α, β, γ) available for substitution to reach critical pockets in HDAC isozymes. Structure-guided substitutions to the tropolone scaffold are expected to achieve potency and selectivity, not only for HDAC enzymes relative to other metalloenzymes, but within individual HDAC isozymes. Class selective inhibitors would also provide valuable probes to better understand the role of different HDACs in cellular regulation and pathologies.

In one aspect, the application provides compounds of Formula (I) and pharmaceutically acceptable salts thereof, where the identity of individual substituents is set forth below.

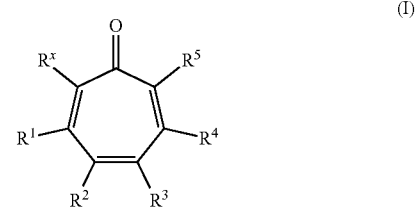

(I)

In another aspect, the application provides methods for the preparation of compounds of Formula (I) and pharmaceutically acceptable salts thereof.

In another aspect, the application provides pharmaceutical compositions comprising a compound of Formula (I) or a pharmaceutically acceptable salt thereof. In one embodiment, the pharmaceutical composition comprises a compound of Formula (I) or a pharmaceutically acceptable salt thereof, and a pharmaceutically acceptable carrier. In another aspect, a method for the preparation of a pharmaceutical composition is provided comprising a compound of Formula (I) or a pharmaceutically acceptable salt thereof.

In another aspect, the application provides methods of treatment comprising administering a compound of Formula (I) or a pharmaceutically acceptable salt thereof, or a pharmaceutical composition comprising a compound of Formula (I) or a pharmaceutically acceptable salt thereof, to a subject, such as a subject having a disease, disorder, or condition.

In another aspect, the application provides methods of treatment comprising administering a compound of Formula (I) or a pharmaceutically acceptable salt thereof, or a pharmaceutical composition comprising a compound of Formula (I) or a pharmaceutically acceptable salt thereof, to a subject having a disease, disorder, or condition or a subject at risk for having a disease, disorder, or condition, wherein the disease, disorder, or condition includes cancers, such as, but not limited to, colon cancer, hematological malignancies and cutaneous T-cell lymphoma.

In another aspect, compounds described herein inhibit HDAC, specifically HDAC-2, HDAC-4 and HDAC-8, activity. Compounds that inhibit HDAC activity are potentially useful in treating certain cancers. The compounds of Formula (I) or pharmaceutically acceptable salts thereof are useful for treating such diseases, disorders, or conditions.

Other aspects and features of the application are described herein.

DETAILED DESCRIPTION

The following definitions are meant to clarify the terms defined. If a particular term used herein is not specifically defined, the term should not be considered to be indefinite. Rather, such undefined terms are to be construed in accordance with their plain and ordinary meaning to skilled artisans in a field of art to which the application is directed.

As used herein the term "alkyl" refers to a fully saturated straight or branched chain hydrocarbon having one to ten carbon atoms, which may be optionally substituted, as herein further described, with multiple degrees of substitution being allowed. Examples of "alkyl" include, but are not limited to, methyl, ethyl, n-propyl, isopropyl, isobutyl, n-butyl, sec-butyl, tert-butyl, isopentyl, n-pentyl, neopentyl, n-hexyl, and 2-ethylhexyl.

The number of carbon atoms in an alkyl group will be represented by the phrase "$C_{x-y}$ alkyl," which refers to an alkyl group, as herein defined, containing from x to y, inclusive, carbon atoms. Thus, $C_{1-6}$ alkyl represents an alkyl chain having from 1 to 6 carbons as described above, and for example, includes, but is not limited to, methyl, ethyl, n-propyl, isopropyl, isobutyl, n-butyl, sec-butyl, tert-butyl, isopentyl, n-pentyl, neopentyl, and n-hexyl.

As used herein, the term "alkylene" refers to a fully saturated straight or branched chain divalent hydrocarbon radical having from one to ten carbon atoms, which may be optionally substituted as herein further described, with multiple degrees of substitution being allowed. Examples of "alkylene" include, but are not limited to, methylene, ethylene, n-propylene, 1-methylethylene, 2-methylethylene, dimethylmethylene, n-butylene, 1-methyl-n-propylene, and 2-methyl-n-propylene.

The number of carbon atoms in an alkylene group will be represented by the phrase "$C_{x-y}$ alkylene," which refers to an alkylene group, as herein defined, containing from x to y, inclusive, carbon atoms. Thus, $C_{1-4}$ alkylene represents an alkylene chain having from 1 to 4 carbons as described above, and for example, includes, but is not limited to, methylene, ethylene, n-propylene, 1-methylethylene, 2-methylethylene, dimethylmethylene, n-butylene, 1-methyl-n-propylene, and 2-methyl-n-propylene.

As used herein, the term "heterocycle" or "heterocyclyl" refers to a mono-, bi-, or tricyclic ring system containing one or more heteroatoms. Such "heterocycle" or "heterocyclyl" groups may be optionally substituted as herein further described, with multiple degrees of substitution being allowed. The terms "heterocycle" or "heterocyclyl," as used herein, do not include ring systems which contain any aromatic rings, but do include ring systems that have one or more degrees of unsaturation. Examples of heteroatoms include nitrogen, oxygen, or sulfur atoms, including N-oxides, sulfur oxides, and sulfur dioxides. Carbon atoms in the ring system can also be optionally oxidized to form heterocyclic rings such as, 2-oxo-pyrrolidin-1-yl or 2-oxo-piperidin-1-yl. Typically, the ring is three- to twelve-membered. Such rings may be optionally fused to one or more of another heterocyclic ring(s) or cycloalkyl ring(s). Examples of "heterocycle" or "heterocyclyl" groups, as used herein, include, but are not limited to, tetrahydrofuran, tetrahydropyran, 1,4-dioxane, 1,3-dioxane, piperidine, pyrrolidine, morpholine, tetrahydrothiopyran, and tetrahydrothiophene, where attachment can occur at any point on said rings, as long as attachment is chemically feasible. Thus, for example, "morpholine" can refer to morpholin-2-yl, morpholin-3-yl, and morpholin-4-yl.

As used herein, when "heterocycle" or "heterocyclyl" is recited as a possible substituent, the "heterocycle" or "heterocyclyl" group can attach through either a carbon atom or any heteroatom, to the extent that attachment at that point is chemically feasible. For example, "heterocyclyl" would include pyrrolidin-1-yl, pyrrolidin-2-yl, and pyrrolidin-3-yl. When "heterocycle" or "heterocyclyl" groups contain a nitrogen atom in the ring, attachment through the nitrogen atom can alternatively be indicated by using an "-ino" suffix with the ring name. For example, pyrrolidino refers to pyrrolidin-1-yl.

As used herein, the term "halogen" refers to fluorine, chlorine, bromine, or iodine.

As used herein, the term "aryl" refers to a six- to ten-membered cyclic, aromatic hydrocarbon, which may be optionally substituted as herein further described, with multiple degrees of substitution being allowed. Examples of "aryl" groups as used herein include, but are not limited to, phenyl and naphthyl. As used herein, the term "aryl" also includes ring systems in which a phenyl or naphthyl group is optionally fused with one to three non-aromatic, saturated or unsaturated, carbocyclic rings. For example, "aryl" would include ring systems such as indene, with attachment possible to either the aromatic or the non-aromatic ring(s). In some embodiments, an aryl group is phenyl, which can be optionally substituted as indicated.

As used herein, the term "heteroaryl" refers to a five- to fourteen-membered optionally substituted mono- or polycyclic ring system, which contains at least one aromatic ring and also contains one or more heteroatoms. Such "heteroaryl" groups may be optionally substituted as herein further described, with multiple degrees of substitution being allowed. In a polycyclic "heteroaryl" group that contains at least one aromatic ring and at least one non-aromatic ring, the aromatic ring(s) need not contain a heteroatom. Thus, for example, "heteroaryl," as used herein, would include indolinyl. Further, the point of attachment may be to any ring within the ring system without regard to whether the ring containing the attachment point is aromatic or contains a heteroatom. Thus, for example, "heteroaryl," as used herein, would include indolin-1-yl, indolin-3-yl, and indolin-5-yl. Examples of heteroatoms include nitrogen, oxygen, or sulfur atoms, including N-oxides, sulfur oxides, and sulfur dioxides, where feasible. Examples of "heteroaryl" groups include, but are not limited to, furyl, thiophenyl, pyrrolyl, oxazolyl, thiazolyl, imidazolyl, isoxazolyl, isothiazolyl, 1,2,4-triazolyl, pyrazolyl, pyridinyl, pyridazinyl, pyrimidinyl, indolyl, isoindolyl, benzo[b]thiophenyl, benzimidazolyl, benzothiazolyl, pteridinyl, and phenazinyl, where attachment can occur at any point on said rings, as long as attachment is chemically feasible. Thus, for example, "thiazolyl" refers to thiazol-2-yl, thiazol-4-yl, and thiaz-5-yl.

As used herein, when "heteroaryl" is recited as a possible substituent, the "heteroaryl" group can attach through either a carbon atom or any heteroatom, to the extent that attachment at that point is chemically feasible.

As used herein, the term "substituted" refers to substitution of one or more hydrogens of the designated moiety with the named substituent or substituents, multiple degrees of substitution being allowed unless otherwise stated, provided that the substitution results in a stable or chemically feasible compound. A stable compound or chemically feasible compound is one in which the chemical structure is not substantially altered when kept at a temperature from about −80° C. to about +40° C., in the absence of moisture or other chemically reactive conditions, for at least a week, or a compound which maintains its integrity long enough to be useful for therapeutic or prophylactic administration to a patient. As used herein, the phrases "substituted with one or more . . . " or "substituted one or more times . . . " refer to a number of substituents that equals from one to the maximum number of substituents possible based on the number of available bonding sites, provided that the above conditions of stability and chemical feasibility are met.

As used herein, the various functional groups represented will be understood to have a point of attachment at the functional group having the hyphen or dash (-) or an asterisk (*). In other words, in the case of —$CH_2CH_2CH_3$, it will be understood that the point of attachment is the $CH_2$ group at the far left. If a substituent group is recited without an asterisk or a dash, then its attachment point is the attachment point that skilled artisans would generally associate with that group. For example, "methyl" is —$CH_3$, as that conforms to the generally understood meaning of what a methyl group is.

When any variable occurs more than one time in any one constituent, or multiple constituents, its definition on each occurrence is independent of its definition on every other occurrence.

As used herein, multi-atom bivalent species are to be read from left to right. For example, if the specification or claims recite A-D-E and D is defined as —OC(O)—, the resulting group with D replaced is: A-OC(O)-E and not A-C(O)O-E.

As used herein, the term "optionally" means that the subsequently described event(s) may or may not occur.

As used herein, "administer" or "administering" means to introduce, such as to introduce to a subject a compound or composition. The term is not limited to any specific mode of delivery, and can include, for example, subcutaneous delivery, intravenous delivery, intramuscular delivery, intracisternal delivery, delivery by infusion techniques, transdermal delivery, oral delivery, nasal delivery, and rectal delivery. Furthermore, depending on the mode of delivery, the administering can be carried out by various individuals, including, for example, a health-care professional (e.g., physician, nurse, etc.), a pharmacist, or the subject (i.e., self-administration).

As used herein, "treat" or "treating" or "treatment" can refer to one or more of: delaying the progress of a disease, disorder, or condition; controlling a disease, disorder, or condition; ameliorating one or more symptoms characteristic of a disease, disorder, or condition; or delaying the recurrence of a disease, disorder, or condition, or characteristic symptoms thereof, depending on the nature of the disease, disorder, or condition and its characteristic symptoms.

As used herein, "subject" refers to any mammal such as, but not limited to, humans, horses, cows, sheep, pigs, mice, rats, dogs, cats, and primates such as chimpanzees, gorillas, and rhesus monkeys. In an embodiment, the "subject" is a human. In another embodiment, the "subject" is a human who exhibits one or more symptoms characteristic of a disease, disorder, or condition. The term "subject" does not require one to have any particular status with respect to a hospital, clinic, or research facility (e.g., as an admitted patient, a study participant, or the like).

As used herein, the term "compound" includes free acids, free bases, and salts thereof. Thus, phrases such as "the compound of embodiment 1" or "the compound of claim 1" are intended to refer to any free acids, free bases, and salts thereof that are encompassed by embodiment 1 or claim 1.

As used herein, "substituted tropolone derivatives" refers to compounds represented by Formula (I) or pharmaceutically acceptable salts thereof, as described in detail below.

As used herein, the term "pharmaceutical composition" is used to denote a composition that may be administered to a mammalian host, e.g., orally, topically, parenterally, by inhalation spray, or rectally, in unit dosage formulations containing conventional non-toxic carriers, diluents, adjuvants, vehicles and the like. The term "parenteral" as used herein, includes subcutaneous injections, intravenous, intramuscular, intracisternal injection, or by infusion techniques.

Also included within the scope of the compositions and methods provided herein are the individual enantiomers of the compounds represented by Formula (I) or pharmaceutically acceptable salts thereof, as well as any wholly or partially racemic mixtures thereof. The compositions and methods also cover the individual enantiomers of the compounds represented by Formula (I) or pharmaceutically acceptable salts thereof, as well as mixtures with diastereoisomers thereof in which one or more stereocenters are inverted. Unless otherwise stated, structures depicted herein are also meant to include compounds which differ only in the presence of one or more isotopically enriched atoms. For example, compounds having the present structure except for the replacement of a hydrogen atom by a deuterium or tritium, or the replacement of a carbon atom by a $^{13}C$— or $^{14}C$-enriched carbon are within the scope of the invention. Formula (I) also implicitly includes any tautomeric forms of the compounds included, even though those forms may not be expressly depicted by the chemical formula.

In several aspects, the present compositions and methods relate to substituted tropolone derivatives, pharmaceutical compositions comprising a substituted tropolone derivative, methods of making a substituted tropolone derivative, methods of making pharmaceutical compositions comprising a substituted tropolone derivative, and methods of using a substituted tropolone derivative or pharmaceutical compositions comprising a substituted tropolone derivative, particularly for the treatment of diseases, disorders, or conditions where inhibition of HDAC is beneficial, such as certain cancers.

In a first aspect, the present composition provides a substituted tropolone derivative or a pharmaceutically acceptable salt thereof. Such compounds are useful in inhibiting the activity of HDAC, as discussed in more detail below.

In a first embodiment (i.e., embodiment 1), the composition provides a compound of Formula (I) or a pharmaceutically acceptable salt thereof:

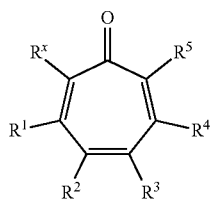

(I)

wherein:

$R^x$ is —$OR^{6a}$, —$NR^{6a}R^{6b}$, —$SR^{6a}$, —$NR^{6a}C(O)R^{6b}$, or —$OC(O)R^{6a}$;

$R^1$, $R^2$, $R^3$, $R^4$, $R^5$, $R^{6a}$, and $R^{6b}$ independently are hydrogen, $C_{1-6}$ alkyl, $C_{3-10}$ cycloalkyl, —$C_{1-6}$alkylene-($C_{3-10}$cycloalkyl), heterocyclyl, —$C_{1-6}$ alkylene-(heterocyclyl), aryl, —$C_{1-6}$ alkylene-(aryl), heteroaryl, or —$C_{1-6}$ alkylene-(heteroaryl), wherein each of the foregoing is optionally substituted 1 to 4 times by $R^7$;

$R^7$ independently is halogen, $C_{1-6}$ alkyl, $C_{3-10}$ cycloalkyl, —$C_{1-6}$ alkylene-($C_{3-10}$ cycloalkyl), heterocyclyl, —$C_{1-6}$ alkylene-(heterocyclyl), phenyl, —$C_{1-6}$ alkylene-(phenyl), heteroaryl, —$C_{1-6}$ alkylene-(heteroaryl), —CN, —$CF_3$, —$OCF_3$, —$OR^a$, —$S(O)_n$—$R^a$, —$SO_2O$—$R^a$, —$NR^aR^b$, —$C(O)R^a$, —$C(O)$—O—$R^a$, —O—$C(O)$—$R^a$, —$C(O)NR^aR^b$, —$NR^aC(O)$—$R^b$, —$OC(O)$—$NR^aR^b$, —$NR^a$—$C(O)$—$OR^b$, or —$NR^aC(O)NR^aR^b$, wherein the alkyl, alkylene, cycloalkyl, heterocyclyl, phenyl, and heteroaryl groups are optionally substituted 1 to 4 times by $R^z$;

$R^a$ and $R^b$ independently are hydrogen, $C_{1-6}$ alkyl, $C_{3-10}$ cycloalkyl, —$C_{1-6}$alkylene-($C_{3-10}$ cycloalkyl), heterocyclyl, —$C_{1-6}$ alkylene-(heterocyclyl), phenyl, —$C_{1-6}$ alkylene-(phenyl), heteroaryl, —$C_{1-6}$ alkylene-(heteroaryl), wherein the alkyl, alkylene, cycloalkyl, heterocyclyl, phenyl, and heteroaryl groups are optionally substituted 1 to 4 times by $R^z$;

or, if $R^a$ and $R^b$ are both attached to the same nitrogen atom, together with that nitrogen atom they may optionally combine to form a heterocyclic ring selected from the group consisting of pyrrolidino, pyrazolidino, imidazolidino, oxazolidino, isoxazolidino, thiazolidino, isothiazolidino, piperidino, piperazino, morpholino, thiomorpholino, azetidino, or azepano, wherein each ring is optionally substituted 1 to 4 times by $R^z$;

$R^z$ is halogen, oxo, $C_{1-6}$ alkyl optionally substituted one or more times by halogen, or —O—$C_{1-6}$ alkyl optionally substituted one or more times by halogen; and n is 0, 1, or 2;

provided that $R^4$ and $R^5$ are not both hydrogen.

Embodiment 2

The compound of embodiment 1, wherein $R^1$ is hydrogen or $C_{1-6}$ alkyl.

Embodiment 3

The compound of embodiment 2, wherein $R^1$ is hydrogen.

Embodiment 4

The compound of any one of embodiments 1 to 3, wherein $R^2$ is hydrogen or $C_{1-6}$ alkyl.

Embodiment 5

The compound of embodiment 4, wherein $R^2$ is hydrogen.

Embodiment 6

The compound of any one of embodiments 1 to 5, wherein $R^3$ is hydrogen or $C_{1-6}$ alkyl.

Embodiment 7

The compound of embodiment 6, wherein $R^3$ is hydrogen.

Embodiment 8

The compound of any one of embodiments 1 to 7, wherein $R^4$ is hydrogen, or $C_{1-6}$ alkyl, or aryl, where the aryl group is optionally substituted one to four times by substituents selected independently from the group consisting of halogen, methoxy, ethoxy, isopropoxy, trifluoromethoxy, trifluoromethyl, methyl, ethyl, and isopropyl.

Embodiment 9

The compound of embodiment 8 wherein $R^4$ is hydrogen.

Embodiment 10

The compound of embodiment 8 wherein $R^4$ is $C_{1-6}$ alkyl.

Embodiment 11

The compound of embodiment 9, wherein $R^4$ is methyl, ethyl, isopropyl, propyl, butyl, sec-butyl, isobutyl, or tert-butyl.

Embodiment 12

The compound of embodiment 8, wherein $R^4$ is aryl, which is optionally substituted 1 to 4 times by substituents selected independently from the group consisting of halogen, methoxy, ethoxy, isopropoxy, trifluoromethoxy, trifluoromethyl, methyl, ethyl, and isopropyl.

Embodiment 13

The compound of embodiment 12, wherein $R^4$ is 1-naphthyl or 2-naphthyl.

Embodiment 14

The compound of embodiment 12, wherein $R^4$ is phenyl, which is optionally substituted 1 to 3 times by methoxy.

Embodiment 15

The compound of any one of embodiments 1 to 14, wherein $R^5$ is hydrogen, or $C_{1-6}$ alkyl, or aryl, where the aryl group is optionally substituted one to four times by substituents selected independently from the group consisting of halogen, methoxy, ethoxy, isopropoxy, trifluoromethoxy, trifluoromethyl, methyl, ethyl, and isopropyl.

Embodiment 16

The compound of embodiment 15 wherein $R^5$ is hydrogen.

Embodiment 17

The compound of embodiment 15 wherein $R^5$ is $C_{1-6}$ alkyl.

Embodiment 18

The compound of embodiment 16, wherein $R^5$ is methyl, ethyl, isopropyl, propyl, butyl, sec-butyl, isobutyl, or tert-butyl.

Embodiment 19

The compound of embodiment 15, wherein $R^5$ is aryl, which is optionally substituted one to four times by substituents selected independently from the group consisting of halogen, methoxy, ethoxy, isopropoxy, trifluoromethoxy, trifluoromethyl, methyl, ethyl, and isopropyl.

Embodiment 20

The compound of embodiment 19, wherein $R^5$ is 1-naphthyl or 2-naphthyl.

Embodiment 21

The compound of embodiment 19, wherein $R^5$ is phenyl, which is optionally substituted 1 to 3 times by methoxy.

Embodiment 22

The compound of embodiment 8, wherein $R^4$ is $C_{3-10}$ cycloaklyl, such as cyclopentyl.

Embodiment 23

The compound of embodiment 8, wherein $R^5$ is $C_{3-10}$ cycloaklyl, such as cyclopentyl.

Embodiment 24

The compound of any one of embodiments 1 to 23, wherein $R^x$ is —$OR^{6a}$.

Embodiment 25

The compound of embodiment 24, wherein $R^x$ is —OH or —$OCH_3$.

Embodiment 26

The compound of embodiment 25, wherein $R^x$ is —OH.

Embodiment 27

The compound of any one of embodiments 1 to 23, wherein $R^x$ is —$NR^{6a}R^{6b}$.

Embodiment 28

The compound of claim 27, wherein $R^x$ is —$NH_2$, —$NHCH_3$, or —$N(CH_3)_2$.

Embodiment 29

The compound of embodiment 27, wherein $R^x$ is —$NH_2$.

Embodiment 30

The compound of any one of embodiments 1 to 29, wherein the compound is in the form of a free acid or free base.

Embodiment 31 the compound of any one of embodiments 1 to 29, wherein the compound is in the form of a pharmaceutically acceptable salt.

General Experimental Section

The routes below illustrate general methods of synthesizing compounds of Formula (I) and/or pharmaceutically acceptable salts thereof. The skilled artisan will appreciate that the compounds described herein could be made by methods other than those specifically described herein, by adaptation of the methods described herein and/or by adaptation of methods known in the art. In general, compounds provided herein may be prepared in a multi-step synthesis, as shown below. All quantities shown are approximate, and are given solely for illustrative purposes. Note that, in some instances, tropolone may be shown in a different tautomeric form than what is shown for Formula (I), above.

General Procedure A

The β-substituted derivatives 11 are available from the unsubstituted dibromoenone 3 through the two-step route shown below in scheme 2.

Scheme 2. Synthesis of tropolones

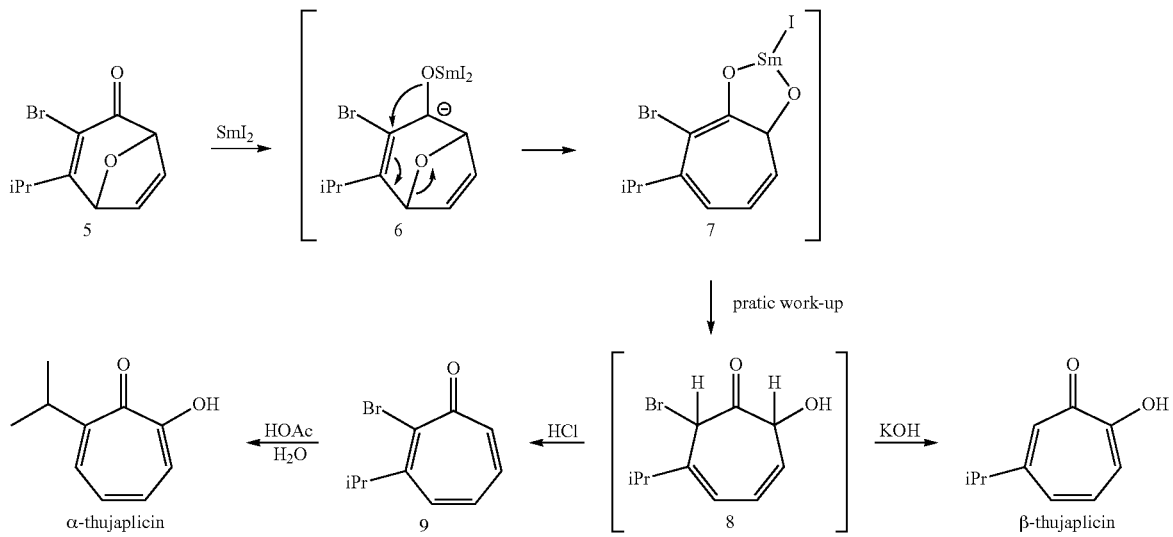

A result was observed when 5 was exposed at low temperatures to samarium(II) iodide in the absence of a proton donor (Scheme 2). Upon mildly acidic work-up, two major products were identified as the bromotropone 9 and β-thujaplicin, demonstrating the potential for a one-pot cleavage/aromatization reaction. It seemed that the two different tropone products arose from a common intermediate 8 that was formed through a regioselective fragmentation of the initial samarium ketyl 6 to give the more stable, extended enolate 7. Initial kinetic protonation would lead to the dieneone 8 that undergoes competitive dehydration or dehydrobromination reactions to give the bromotropone or tropolone product respectively. Careful optimization of reaction conditions allowed complete control over the course of the reaction. When the samarium reduction was quenched with hydroxide, β-thujaplicin was formed as the exclusive product. Alternatively, strong acidic quench (2N HCl) led exclusively to the bromotropone that was directly hydrolyzed to yield the regioisomeric α-thujaplicin. This newly developed methodology provides access to both α- and β-substituted tropolones from a common intermediate 5.

General Procedure B

γ- and β,γ-disubstituted systems are accessed from various 2-substituted furans through a modification of the methodology (Scheme 3, shown below). Furans substituted at C2 (12, R₁≠H) readily react in the TBCP cycloaddition reaction and undergo regioselective hydrolysis to produce the distal ketones 13 as the major isomer (typically greater than 6:1). An approach to γ-substituted systems requires either an initial reduction or substitution of the β-bromide to give 14 or 16 respectively that will be taken on to 15/17 by reaction with samarium iodide.

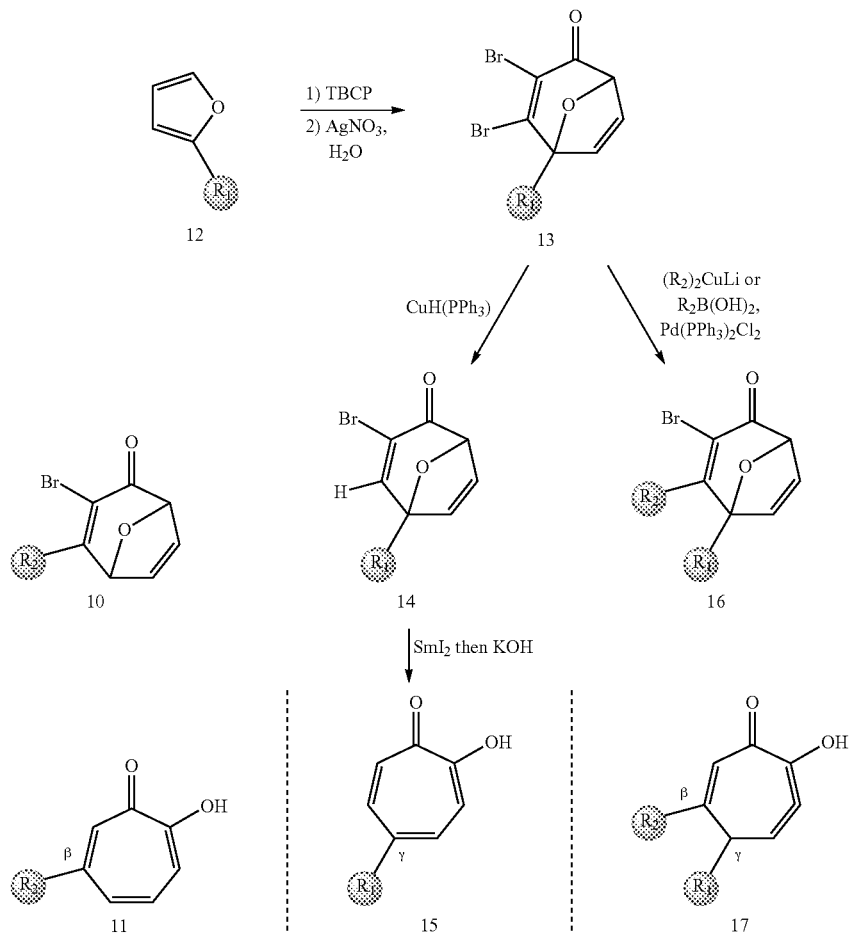

General Procedure C

Substitution at the α-position are a means to introduce isozyme selectivity and are incorporated into analogs already optimized at the β- and γ-positions. One can take advantage of the acidic work-up variant that initially delivers the α-bromotropone that can be readily hydrolyzed to the corresponding tropolone. Three patterns: α,β and α,γ-disubstituted and α,β,γ-trisubstituted systems, are presented (Scheme 4, shown below).

Scheme 4. Synthesis of tropolones with α-substitutions

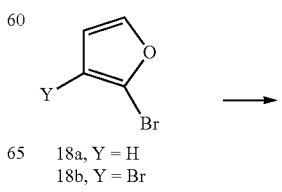

18a, Y = H
18b, Y = Br

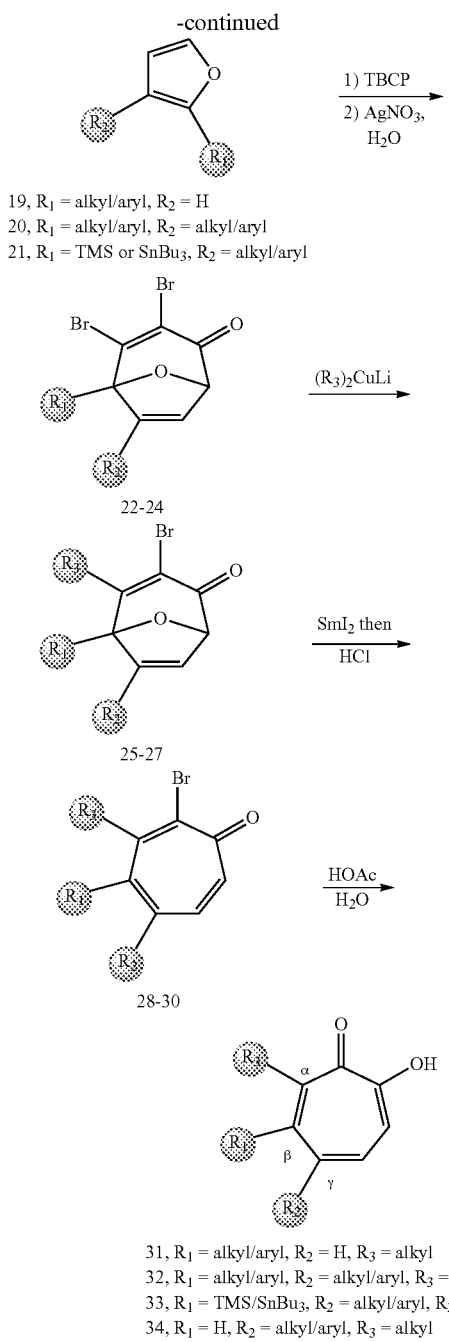

19, R₁ = alkyl/aryl, R₂ = H
20, R₁ = alkyl/aryl, R₂ = alkyl/aryl
21, R₁ = TMS or SnBu₃, R₂ = alkyl/aryl 22-24

25-27

28-30

31, R₁ = alkyl/aryl, R₂ = H, R₃ = alkyl
32, R₁ = alkyl/aryl, R₂ = alkyl/aryl, R₃ = alkyl
33, R₁ = TMS/SnBu₃, R₂ = alkyl/aryl, R₃ = alkyl
34, R₁ = H, R₂ = alkyl/aryl, R₃ = alkyl With this alternate route, the substituent introduced at the β-position of the dibromoenone will ultimately end up at the α-position of the tropolone while the β- and γ-groups will be pre-installed onto the starting furan. Use of a 2-substituted furan 19 in the cycloaddition/hydrolysis sequence will deliver 25 after introduction of the nascent α-substituent by interconversion of the β-bromide. Reductive opening with the acidic work-up and subsequent hydrolysis will give α,β-disubstituted tropolones such as 31. A similar protocol can be used to access the trisubstituted systems commencing with readily available 2,3-dibromofuran 18b. This compound can be selectively functionalized at the C2-position and then reacted in an analogous manner to introduce a C3 substituent as in 20. Conversion to the tropolone follows to give the trisubstituted tropolones 32. Synthesis of the final class, the α,γ-disubstituted will require the introduction of temporary blocking groups.

Although these analogues could simply be derived from various 3-substituted furans there would be little or no selectivity during hydrolysis of the intermediate tetrabromide, leading to a mixture of isomeric ketones which would require separation. A temporary blocking group at C2 to allow regio-controlled formation of the ketone is installed. 2,3-Dibromofuran 18b will be elaborated in two steps to either a 2-silyl- or 2-thiophenyl-3-substituted derivative 21 and converted to the bicyclic adduct as before. The use of silyl or stanyl groups at the 2-position of furan in these cyloadditions can be used, as similarly functionalized furans have been used in Diels-Alder reactions, which is the first step in the TBCP reaction. Buffered hydrolysis of the primary adduct will be controlled by the temporary bridgehead group to produce the desired regioisomer 24 which will be taken via 27 to the tropolones 33. It is not clear if the temporary groups would survive the combination of samarium iodide and acid and may be lost en route to 33 to give the desired compounds 34. If these groups stay intact, they can be removed from the final tropolone under standard conditions. Collectively, the methods described above will give a high degree of control over the substitution pattern of tropolone derivatives.

General Procedure D

All reactions were carried out under an inert argon atmosphere with dry solvents under anhydrous conditions unless otherwise stated. Commercial grade reagents and solvents were used without further purification except as indicated below. Hexanes, tetrahydrofuran (THF), diethyl ether ($Et_2O$), and dichloromethane ($CH_2Cl_2$) were used directly from a Baker cycle-taMer system. Reagents were purchased at the highest commercial quality and used without further purification, unless otherwise noted. Yields refer to chromatographically and spectroscopically ($^1H$ NMR) homogenous materials, unless otherwise stated. Reactions were monitored by thin layer chromatography (TLC) carried out on Whatman silica 60 Å precoated plates using UV light as the visualizing agent and an acidic mixture of anisaldehyde or basic aqueous potassium permanganate ($KMnO_4$) and heated as developing agents. Flash chromatography was performed using Baker silica gel (60 Å particle size). NMR spectra were recorded on Bruker-500 and 400 instruments and calibrated using residual undeuterated solvent as internal reference ($CHCl_3$ at δ 7.27 ppm $^1H$ NMR, δ 77.0 ppm $^{13}C$ NMR; $CD_2Cl_2$ at δ 5.32 ppm $^1H$ NMR, δ 54 ppm $^{13}C$ NMR). The following abbreviations were used to explain the multiplicities: s=singlet, d=doublet, t=triplet, q=quartet, m=multiplet, b=broad. IR spectra were recorded on Shimadzu FT-IR 8400 spectrometer. Melting points (m.p.) are uncorrected and were recorded on a Mel-Temp digital melting point apparatus. High resolution mass spectra (HRMS) were obtained from the University of Connecticut Spectral Facility by electrospray ionization of flight reflectron experiments.

General Procedure E—Suzuki Coupling

2-Chloro-2,4,6-cycloheptatrien-1-one (1.0 eq), aryl boronic acid (2.0 eq), and cesium carbonate (4.0 eq) were added to 10:1 THF/$H_2O$ (0.2 M) and the mixture was thoroughly degassed by bubbling argon through solution (10 min). Bis(triphenylphosphine)palladium(II) dichloride (0.1 eq) was added and the mixture was again degassed with argon. The homogenous solution was heated at 75° C. for 16 h before being cooled to room temperature. Water was added and the mixture was extracted with EtOAc (3×15 mL). The combined organic layers were washed with brine (25 mL), dried over Na$_2$SO$_4$, filtered and concentrated in vacuo. Flash chromatography of the crude residue (SiO$_2$, EtOAc in hexanes) provided the desired α-tropones.

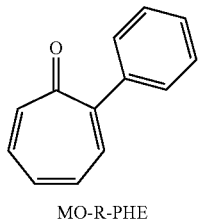 [SMILES: O=c1cccccc1-c1ccccc1]

MO-R-PHE

R$_f$ (0.5, 1:1 EtOAc:Hexanes), M$_p$ (77.9-79.2° C.), >99% yield. IR (KBr): v: 3101, 3022, 1895, 1808, 1625, 1547, 1441, 1261, 784, 698. H$^1$ NMR (500 MHz, CDCl$_3$) δ 7.51-7.49 (m, 2H), 7.43-7.36 (m, 4H), 7.20 (d, J=12.2 Hz, 1H), 7.14 (ddd, J=19.8, 1.3, 1.3, 1.3, 1.4 Hz, 1H), 7.07-7.03 (m, 1H), 6.99-6.95 (m, 1H). C$^{13}$ NMR (126 MHz, CDCl$_3$) δ 186.4, 152.4, 142.2, 139.9, 136.5, 135.2, 133.7, 133.2, 129.0, 128.3, 128.0. HRMS (ESI) calcd for C$_{13}$H$_{11}$O [M+H]$^+$: 183.0810; found: 183.0788.

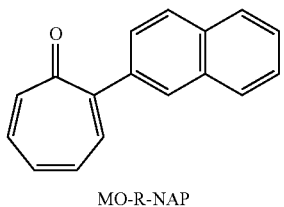 [SMILES: O=c1cccccc1-c1ccc2ccccc2c1]

MO-R-NAP

R$_f$ (0.58, 1:1 EtOAc:Hexanes), M$_p$ (N/A), 97.8% yield. IR (KBr): v: 3056, 3009, 2359, 1926, 1876, 1771, 1703, 1626, 1574, 800, 777, 733, 697. H$^1$ NMR (500 MHz, CDCl$_3$) δ 7.92 (d, J=1.45 Hz, 1H), 7.90 (d, J=2.0 Hz, 1H), 7.71 (d, J=8.3 Hz, 1H), 7.57-7.45 (m, 3H), 7.41 (dd, J=6.9, 0.85, 0.90 Hz, 1H), 7.38-7.36 (m, 1H), 7.26 (d, J=12.1 Hz, 1H), 7.20-7.16 (m, 1H), 6.99-6.97 (m, 2H). C$^{13}$ NMR (126 MHz, CDCl$_3$) δ 186.4, 152.6, 141.7, 138.3, 137.6, 135.5, 133.8, 133.5, 133.2, 130.7, 128.3, 128.2, 126.4, 125.9, 125.6, 125.2, 125.2. HRMS (ESI) calcd for C$_{17}$H$_{13}$O [M+H]$^+$: 233.0966; found: 233.0945.

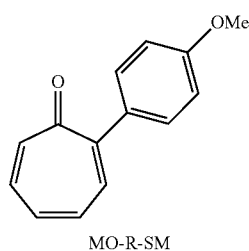

MO-R-SM

R$_f$ (0.59, 1:1 EtOAc:Hexanes), M$_p$ (52.2-53.6° C.), 99.2% yield. IR (KBr): v: 2958, 2835, 2541, 2041, 1974, 1883, 1622, 1564, 1175, 1031, 830, 780, 686. H$^1$ NMR (500 MHz, CDCl$_3$) δ 7.51 (d, J=2.0 Hz, 1H), 7.50 (d, J=2.0 Hz, 1H), 7.40 (d, J=9.0 Hz, 1H), 7.23 (d, J=12.1 Hz, 1H), 7.15 (ddd, J=21.5, 1.2, 1.2, 1.2, 1.2 Hz, 1H), 7.06 (t, J=20.0, 10.1, 9.5 Hz, 1H), 6.99-6.94 (m, 3H), 3.85 (s, 3H). C$^{13}$ NMR (126 MHz, CDCl$_3$) δ 186.5, 159.9, 152.0, 142.0, 136.0, 135.3, 133.8, 132.8, 132.1, 130.6, 113.6, 55.3. HRMS (ESI) calcd for C$_{14}$H$_{13}$O$_2$ [M+H]$^+$: 213.0916; found: 213.0898.

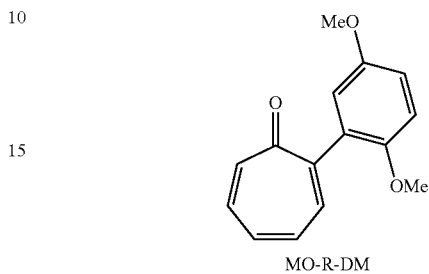

MO-R-DM

R$_f$ (0.29, 1:1 EtOAc:Hexanes), M$_p$ (102.2-103.2° C.), 96.2% yield. IR (KBr): v: 2940, 2832, 2351, 1628, 1588, 1218, 1046, 808, 748, 694. H$^1$ NMR (500 MHz, CDCl$_3$) δ 7.30 (dd, J=8.4, 1.0, 1.1 Hz, 1H), 7.15-7.13 (m, 2H), 7.03-6.94 (m, 2H), 6.88 (s, 1H), 6.88 (s, 1H), 6.82 (t, J=3.2, 1.6, 1.6 Hz, 1H), 3.79 (s, 3H), 3.74 (s, 3H). C$^{13}$ NMR (126 MHz, CDCl$_3$) δ 186.5, 153.7, 150.9, 150.3, 141.0, 136.3, 134.9, 133.5, 133.3, 130.9, 116.4, 114.1, 112.5, 56.5, 55.7. HRMS (ESI) calcd for C$_{15}$H$_{15}$O$_3$ [M+H]$^+$: 243.1021; found: 243.1016.

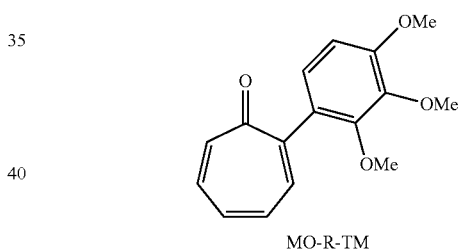

MO-R-TM

R$_f$ (0.29, 1:1 EtOAc:Hexanes), M$_p$ (98.3-99.6° C.), IR, 527.54 mg, 90.8% yield. IR (KBr): v: 2946, 2841, 2825, 1947, 1883, 1626, 1583, 1458, 1103, 1072, 1013, 799, 684. H$^1$ NMR (500 MHz, CDCl$_3$) δ 7.28 (dd, J=9.6, 1.1, 1.1 Hz, 1H), 7.18-7.12 (m, 2H), 7.03-6.93 (m, 3H), 6.72 (d, J=8.5 Hz, 1H), 3.89 (s, 3H), 3.88 (s, 3H), 3.82 (s, 3H). C$^{13}$ NMR (126 MHz, CDCl$_3$) δ 187.0, 154.2, 150.7, 150.6, 141.9, 140.6, 136.3, 135.1, 133.6, 133.1, 127.7, 124.6, 107.3, 60.9, 60.7, 56.0. HRMS (ESI) calcd for C$_{16}$H$_{17}$O$_4$ [M+H]$^+$: 273.1127; found: 273.1118.

General Procedure F—α-Amination

To a solution of α-aryl-tropone (1.0 eq) in EtOH (0.2 M) was added 65% hydrazine monohydrate (25 eq). The solution was allowed to stir at room temperature until all starting material was consumed by monitoring on TLC (~45 min). The reaction was concentrated in vacuo and then taken up in EtOAc (0.05 M) and washed with H$_2$O (3×15 mL). The organic layer was then washed with brine (25 mL), dried over Na$_2$SO$_4$, filtered and concentrated in vacuo. Flash chromatography of the crude residue (SiO$_2$, EtOAc in hexanes) provided the desired α-amino-tropones.

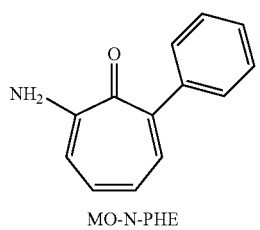 [SMILES: Nc1ccccc(-c2ccccc2)c1=O]

MO-N-PHE $R_f$ (0.61, 4:1 EtOAc:Hexanes), $M_p$ (209.3-210.4° C.), 88.3% yield. IR (KBr): v: 3403, 3251, 3122, 1604, 1515, 1428, 1336, 1235, 1054, 919, 686. $H^1$ NMR (500 MHz, $CD_2Cl_2$) δ 7.50-7.38 (m, 5H), 7.33 (t, J=14.4, 7.1, 7.3 Hz, 1H), 7.14 (t, J=20.2, 10.1, 10.1 Hz, 1H), 6.93 (d, J=10.0 Hz, 1H), 6.77 (t, J=19.6, 9.8, 9.8 Hz, 1H), 6.12 (s, 2H). $C^{13}$ NMR (126 MHz, $CD_2Cl_2$) δ 174.9, 158.5, 143.4, 142.5, 139.0, 135.8, 130.1, 128.3, 127.7, 123.4, 112.7. HRMS (ESI) calcd for $C_{13}H_{12}NO$ $[M+H]^+$: 198.0919; found: 198.0900.

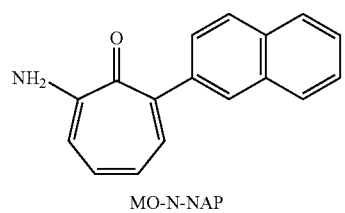 [SMILES: Nc1ccccc(-c2ccc3ccccc3c2)c1=O]

MO-N-NAP $R_f$ (0.63, 4:1 EtOAc:Hexanes), $M_p$ (221.7-222.5° C.), 89.2% yield. IR (KBr): v: 3443, 3280, 3150, 1604, 1511, 1446, 1062, 780, 737. $H^1$ NMR (500 MHz, $CD_2Cl_2$) δ 7.90 (d, J=8.2 Hz, 1H), 7.87 (d, J=8.3 Hz, 1H), 7.55-7.45 (m, 4H), 7.38-7.35 (m, 2H), 7.23 (td, J=20.2, 10.1, 10.1, 1.1, 1.1, 1.1 Hz, 1H), 6.98 (d, J=9.9 Hz, 1H), 6.80 (t, J=19, 9.5, 9.5 Hz, 1H), 6.13 (s, 2H). $C^{13}$ NMR (126 MHz, $CD_2Cl_2$) δ 175.2, 157.9, 141.8, 141.8, 139.6, 136.5, 134.0, 132.2, 128.8, 128.1, 126.9, 126.4, 126.3, 126.2, 126.1, 123.2, 112.8. HRMS (ESI) calcd for $C_{17}H_{14}NO$ $[M+H]^+$: 248.1075; found: 248.1065.

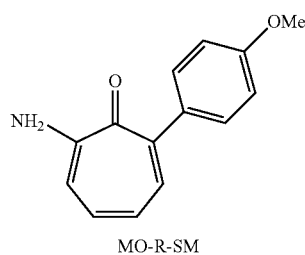

MO-R-SM $R_f$ (0.55, 4:1 EtOAc:Hexanes) $M_p$ (153.8-155.2° C.), 87.2% yield. IR (KBr): v: 3434, 3269, 3233, 2962, 1601, 1511, 1450, 1244, 1023, 829, 781. $H^1$ NMR (500 MHz, $CD_2Cl_2$) δ 7.49 (dd, J=9.6, 1.0, 0.9 Hz, 1H), 7.44-7.41 (m, 2H), 7.10 (td, J=20.0, 1.0, 1.0, 1.0 Hz, 1H), 6.96-6.93 (m, 2H), 6.89 (d, J=10.0 Hz, 1H), 6.24 (s, 2H), 3.83 (s, 3H). $C^{13}$ NMR (126 MHz, $CD_2Cl_2$) δ 174.9, 159.5, 158.4, 141.9, 138.7, 135.6, 135.4, 131.3, 123.3, 113.7, 112.9, 55.8. HRMS (ESI) calcd for $C_{14}H_{14}NO_2$ $[M+H]^+$: 228.1025; found: 228.1018.

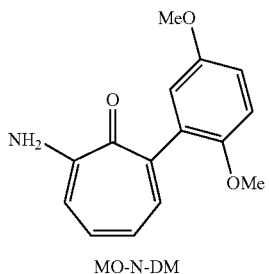

MO-N-DM $R_f$ (0.39, 4:1 EtOAc:Hexanes), $M_p$ (109.6-110.7° C.), 84.6% yield. IR (KBr): v: 3278, 3191, 2939, 2831, 1601, 1519, 1455, 1219, 1047, 783, 725. $H^1$ NMR (500 MHz, $CD_2Cl_2$) δ 7.39 (d, J=9.5 Hz, 1H), 7.12 (t, J=20.2, 10.1, 10.1 Hz, 1H), 6.92-6.87 (m, 3H), 6.80 (d, J=2.9 Hz, 1H), 6.72 (t, J=19.5, 9.7, 9.8 Hz, 1H), 6.42 (s, 2H), 3.77 (s, 3H), 3.69 (s, 3H). $C^{13}$ NMR (126 MHz, $CD_2Cl_2$) δ 174.5, 158.1, 154.1, 151.5, 139.8, 138.9 136.2, 133.9, 122.6, 117.1, 113.4, 112.9, 112.6, 56.7, 56.2. HRMS (ESI) calcd for $C_{15}H_{16}NO_3$ $[M+H]^+$: 258.1130; found: 258.1151.

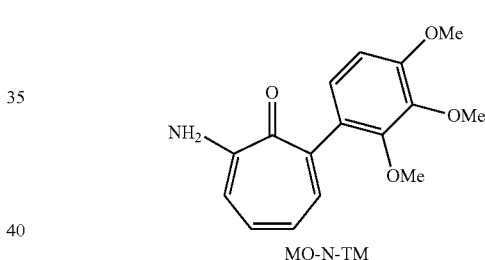

MO-N-TM $R_f$ (0.42, 4:1 EtOAc:Hexanes), $M_p$ (175.3-176.5° C.), 86.4% yield. IR (KBr): v: 3367, 2939, 2825, 1599, 1514, 1455, 1097, 1019, 770. $H^1$ NMR (500 MHz, $CDCl_3$) δ 7.41 (d, J=9.5 Hz, 1H), 7.09 (t, J=20.1, 10.0, 10.1 Hz, 1H), 6.91 (d, J=8.5 Hz, 1H), 6.87 (d, J=10 Hz, 1H), 6.72-6.68 (m, 2H), 6.28 (s, 2H), 3.99 (s, 3H), 3.87 (s, 3H), 3.73 (s, 3H). $C^{13}$ NMR (126 MHz, $CDCl_3$) δ 174.4, 157.2, 153.1, 151.3, 142.0, 139.3, 138.7, 135.4, 129.7, 124.5, 122.4, 112.4, 107.4, 60.9, 60.7, 55.9. HRMS (ESI) calcd for $C_{16}H_{18}NO_4$ $[M+H]^+$: 288.1236; found: 288.1217.

General Procedure G—α-Amino Tropone Hydrolysis

The α-amino-tropone (1.0 eq) was dissolved in 1:1 EtOH:$H_2O$ (2.0 M) to which was added 2 N KOH (20 eq). The reaction was heated to 100° C. and stirred for 16 h. The reaction was returned to room temperature and diluted with 15% NaOH. The aqueous layer was washed with $Et_2O$ (3×15 mL) and $CH_2Cl_2$ (3×15 mL) and then acidified to pH 2.0 and extracted with $CH_2Cl_2$ (3×15 mL). The $CH_2Cl_2$ solution was washed with brine, dried over $Na_2SO_4$, filtered and concentrated in vacuo.

(Example 1)

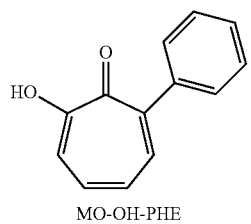

MO-OH-PHE $R_f$ (0.52, 1:19 iPrOH:CH$_2$Cl$_2$), M$_p$ (N/A), 89.6% yield. IR (KBr): v: 3200-2800 broad, 2917, 2848, 1721, 1712, 1615, 1595, 1548, 1417, 1247, 737, 698. H$^1$ NMR (500 MHz, CD$_2$Cl$_2$) δ 7.60 (d, J=9.9 Hz, 1H), 7.51 (d, J=7.4 Hz, 2H), 7.46 (t, J=14.8, 7.2, 7.6 Hz, 2H), 7.42-7.39 (m, 3H), 7.10 (t, J=17.2, 7.7, 9.5 Hz, 1H). C$^{13}$ NMR (126 MHz, CD$_2$Cl$_2$) δ 171.9, 170.8, 141.1, 140.7, 139.5, 137.3, 129.8, 128.7, 128.6, 127.9, 122.0. HRMS (ESI) calcd for C$_{13}$H$_{11}$O$_2$ [M+H]$^+$: 199.0759; found: 199.0749.

(Example 2)

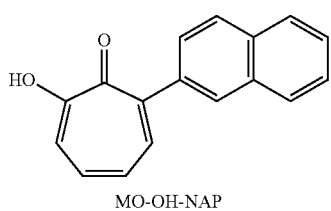

MO-OH-NAP $R_f$ (0.52, 1:19 iPrOH:CH$_2$Cl$_2$), M$_p$ (N/A), 90.5% yield. IR (KBr): v: 3200-2800 broad, 3173, 3044, 2925, 1614, 1593, 1548, 1470, 1367, 1258, 1242, 1210, 800, 773, 689. H$^1$ NMR (500 MHz, CD$_2$Cl$_2$) δ 7.96 (d, J=7.3 Hz, 2H), 7.61-7.50 (m, 6H), 7.44 (t, J=14.0, 6.9, 7.1 Hz, 2H), 7.13-7.09 (m, 1H). C$^{13}$ NMR (126 MHz, CD$_2$Cl$_2$) δ 171.6, 170.8, 141.6, 138.6, 138.2, 137.2, 134.1, 131.5, 129.0, 128.9, 127.8, 127.0, 126.7, 126.5, 126.0, 125.9, 123.8. HRMS (ESI) calcd for C$_{12}$H$_{13}$O$_2$ [M+H]$^+$: 249.0916; found: 249.0928.

(Example 3)

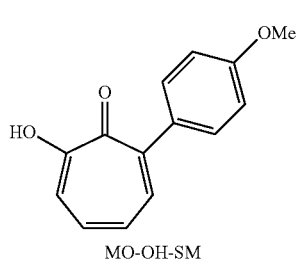

MO-OH-SM $R_f$ (0.52, 1:19 iPrOH:CH$_2$Cl$_2$), M$_p$ (N/A), 92.2% yield. IR (KBr): v: 3200-2800 broad, 3128, 3927, 1920, 1802, 1615, 1593, 1499, 1367, 1039, 802, 728. H$^1$ NMR (500 MHz, CD$_2$Cl$_2$) δ 7.49 (d, J=10.0 Hz, 1H), 7.42-7.39 (m, 3H), 7.22 (dd, J=7.4, 1.5, 1.5 Hz, 1H), 7.07-7.02 (m, 3H), 3.76 (s, 3H). C$^{13}$ NMR (126 MHz, CD$_2$Cl$_2$) δ 171.2, 170.9, 157.1, 141.4, 137.5, 136.5, 130.7, 130.1, 129.8, 127.4, 122.6, 121.0, 111.7, 56.1. HRMS (ESI) calcd for C$_{14}$H$_{13}$O$_3$ [M+H]$^+$: 229.0865; found: 229.0854.

(Example 4)

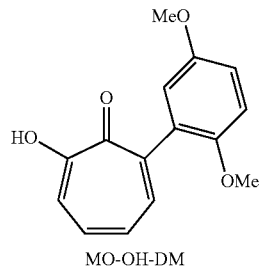

MO-OH-DM $R_f$ (0.52, 1:19 iPrOH:CH$_2$Cl$_2$), M$_p$ (N/A), 89.3% yield. IR (KBr): v: 3200-2800 broad, 2930, 2832, 2002, 1925, 1797, 1615, 1595, 1548, 1496, 1398, 1201, 1044, 1024, 805, 728. H$^1$ NMR (500 MHz, CD$_2$Cl$_2$) δ 7.49 (d, J=10 Hz, 1H), 7.39-7.37 (m, 2H), 7.07-7.03 (m, 1H), 6.97-6.92 (m, 2H), 6.82 (d, J=2.7 Hz, 1H), 3.79 (s, 3H), 3.71 (s, 3H). C$^{13}$ NMR (126 MHz, CD$_2$Cl$_2$) δ 171.1, 170.9, 154.1, 151.3, 141.3, 137.6, 136.3, 130.7, 127.4, 122.6, 116.7, 114.4, 112.9, 56.8, 56.2. HRMS (ESI) calcd for C$_{15}$H$_{15}$O$_4$ [M+H]$^+$: 259.0970; found: 259.0956.

(Example 5)

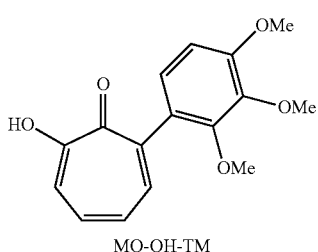

MO-OH-TM $R_f$ (0.55, 1:19 iPrOH:CH$_2$Cl$_2$), M$_p$ (N/A), 88.7% yield. IR (KBr): v: 3200-2800 broad, 2994, 2938, 2837, 1992, 1920, 1713, 1614, 1596, 1408, 1301, 1108, 1046, 793, 735. H$^1$ NMR (500 MHz, CD$_2$Cl$_2$) δ 7.49 (d, J=10 Hz, 1H), 7.40-7.36 (m, 2H), 7.07-7.01 (m, 1H), 6.93 (d, J=8.6 Hz, 1H), 6.77 (d, J=8.6 Hz, 1H), 3.89 (s, 3H), 3.89 (s, 3H), 3.74 (s, 3H). C$^{13}$ NMR (126 MHz, CD$_2$Cl$_2$) δ 171.9, 170.4, 154.6, 151.8, 142.7, 141.4, 173.3, 136.8, 127.5, 127.4, 124.8, 122.2, 107.8, 61.4, 61.1, 56.5. HRMS (ESI) calcd for C$_{16}$H$_{12}$O$_5$ [M+H]$^+$: 289.1076; found: 289.1103.

Example Compounds

Examples of compounds of Formula (I) or pharmaceutically acceptable salts thereof are described below. These compounds were made according to the general procedures described above. Each of the identified compounds constitutes a separate embodiment of the invention, where the embodiment includes the compound in its free (non-salted) form and pharmaceutically acceptable salts of the free compound. Each of the recited compounds in its free (non-salted) form constitutes a separate embodiment of the invention. In addition, the pharmaceutically acceptable salts of each of the recited compounds constitute a separate embodiment of the invention. In other embodiments, the hydrochloride salts of each of the recited compounds constitute a separate embodiment of the invention.

TABLE 1

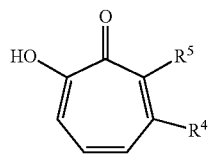

| Ex. | $R^5$ Substituent | $R^4$ Substituent | $K_i$ HDAC-8 (nM) | $K_i$ HDAC-4 (nM) | $IC_{50}$ Jurkat (μM) | $IC_{50}$ HuT-78 (μM) |
|---|---|---|---|---|---|---|
| 1 | Phenyl | H | 0.17 | 0.08 | 3.33 | 7.83 |
| 2 | 2-naphthyl | H | 7.63 | 0.54 | | |
| 3 | 4-methoxyphenyl | H | 0.14 | 2.74 | 0.62 | 2.87 |
| 4 | 2,5-dimethoxyphenyl | H | 0.44 | 183.95 | 0.75 | 3.05 |
| 5 | 2,3,4-trimethoxyphenyl | H | 0.04 | 59.02 | 1.86 | 4.74 |
| 6 | H | phenyl | 19.36 | 72.84 | 0.67 | 4.14 |
| 7 | H | 3-methoxyphenyl | 1.36 | 1.70 | 4.62 | 8.95 |
| 8 | H | 2,5-dimethoxyphenyl | 1.42 | 540.78 | 5.88 | 17.09 |
| 9 | H | isopropyl | 105.36 | 3.32 | 1.10 | 4.99 |
| 10 | H | tert-butyl | 2.69 | 488.90 | 4.45 | 13.11 |
| 11 | H | sec-butyl | 10.13 | 94.45 | 0.59 | 3.25 |
| 12 | H | cyclopentyl | 23.28 | 6.64 | 6.30 | 11.36 |

Compounds in Table 1 having a basic or acidic group are depicted as the free acid or base. Depending on the reaction conditions or purification conditions, various compounds of Table 1 having a basic or acidic group may have been isolated as a free acid or base, or as a salt (e.g., a hydrochloride salt), or both.

The example compounds of Table 1 inhibit HDAC, specifically HDAC-2, HDAC-4 and HDAC-8, activity. Compounds that inhibit HDAC activity are potentially useful in treating certain cancers. The compounds of Formula (I) or pharmaceutically acceptable salts thereof are therefore useful for treating such diseases, disorders, or conditions.

Pharmaceutical Compositions

In some embodiments, a pharmaceutical composition is provided comprising a compound of Formula (I) or a pharmaceutically acceptable salt thereof. In some such embodiments, the pharmaceutical composition is a solid pharmaceutical composition. In some embodiments, the solid pharmaceutical composition comprises a compound of Formula (I) or a pharmaceutically acceptable salt thereof and a pharmaceutically acceptable carrier. In some such embodiments, the solid pharmaceutical composition can further comprise one or more pharmaceutically acceptable excipients and/or one or more pharmaceutically acceptable diluents. In some embodiments, a solid pharmaceutical composition is provided in unit dosage form comprising from 0.01 mg to 1000 mg of a compound of Formula (I) or a pharmaceutically acceptable salt thereof and a pharmaceutically acceptable carrier.

In some other embodiments, the pharmaceutical composition is a liquid pharmaceutical composition comprising a compound of Formula (I) or a pharmaceutically acceptable salt thereof and a liquid carrier. In some embodiments, the liquid carrier is an aqueous medium. In some embodiments, the liquid pharmaceutical composition comprises from 100 μg/mL to 500 mg/mL of a compound of Formula (I) or a pharmaceutically acceptable salt thereof. In some such embodiments, the pharmaceutically acceptable carrier is an aqueous medium. In some such embodiments, the pharmaceutically acceptable carrier is water.

In an embodiment, the pharmaceutical compositions comprising a compound of Formula (I) or a pharmaceutically acceptable salt thereof may be in a form suitable for oral use, for example, as tablets, troches, lozenges, aqueous, or oily suspensions, dispersible powders or granules, emulsions, hard or soft capsules, or syrups or elixirs. Compositions intended for oral use may be prepared according to any known method, and such compositions may contain one or more agents selected from the group consisting of sweetening agents, flavoring agents, coloring agents, and preserving agents in order to provide pharmaceutically elegant and palatable preparations. Tablets may contain the active ingredient in admixture with non-toxic pharmaceutically-acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch or alginic acid; binding agents, for example, starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,356,108; 4,166,452; and 4,265,874, to form osmotic therapeutic tablets for controlled release.

In another embodiment, formulations for oral use may also be presented as hard gelatin capsules where the active ingredient is mixed with an inert solid diluent, for example, calcium carbonate, calcium phosphate or kaolin, or a soft gelatin capsules wherein the active ingredient is mixed with water or an oil medium, for example peanut oil, liquid paraffin, or olive oil.

Also, oily suspensions may be formulated by suspending the active ingredient in a vegetable oil, for example arachis oil, olive oil, sesame oil or coconut oil, or in a mineral oil such as a liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above. Additional excipients, for example, sweetening, flavoring, and coloring agents may also be present.

The pharmaceutical composition provided herein may also be in the form of oil-in-water emulsions. The oily phase may be a vegetable oil, for example, olive oil or arachis oil, or a mineral oil, for example a liquid paraffin, or a mixture thereof. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of said partial esters with ethylene oxide, for example polyoxyethylene sorbitan monooleate. The emulsions may also contain sweetening and flavoring agents.

In another embodiment, the pharmaceutical compositions provided herein may comprise a syrup or elixir. Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known methods using suitable dispersing or wetting agents and suspending agents described above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution, and isotonic sodium chloride solution. In addition, sterile, fixed oils are conveniently employed as solvent or suspending medium. For this purpose, any bland fixed oil may be employed using synthetic mono- or diglycerides. In addition, fatty acids such as oleic acid find use in the preparation of injectables.

In an embodiment, the pharmaceutical compositions provided herein may comprise an aqueous solution, where the solution comprises the active ingredient in a solubilized form. In some such embodiments, the pharmaceutical composition may also contain an amount of non-solubilized active ingredient (e.g., suspended in the aqueous solution). In other such embodiments, the pharmaceutical composition contains the active ingredient such that substantially all of the active ingredient is solubilized in the aqueous solution (e.g., at least 95%, or at least 97%, or at least 99%, or at least 99.5%, or at least 99.8% (by moles) based on the total amount of active ingredient present in the pharmaceutical composition. In some embodiments, the active ingredient is contained within a liposome, which is suspended in a suitable medium, such as an aqueous medium. Such liposomal delivery systems are well known in the art.

Pharmaceutically-acceptable salts of compounds of Formula (I), where a basic or acidic group is present in the structure, are also included within the scope of the invention. The term "pharmaceutically acceptable salts" refers to salts of the compounds of this invention which are not biologically or otherwise undesirable and are generally prepared by reacting the free base with a suitable organic or inorganic acid or by reacting the acid with a suitable organic or inorganic base. Representative salts include the following salts: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, laurate, malate, maleate, mandelate, mesylate, methylbromide, methylnitrate, methylsulfate, monopotassium maleate, mucate, napsylate, nitrate, N-methylglucamine, oxalate, pamoate (embonate), palmitate, pantothenate, phosphate/diphosphate, polygalacturonate, potassium, salicylate, sodium, stearate, subacetate, succinate, tannate, tartrate, teoclate, tosylate, triethiodide, trimethylammonium, and valerate. When an acidic substituent is present, such as —COOH, there can be formed the ammonium, morpholinium, sodium, potassium, barium, calcium salt, and the like, for use as the dosage form. When a basic group is present, such as amino or a basic heteroaryl radical, such as pyridyl, there can be formed an acidic salt, such as hydrochloride, hydrobromide, phosphate, sulfate, trifluoroacetate, trichloroacetate, acetate, oxalate, maleate, pyruvate, malonate, succinate, citrate, tartarate, fumarate, mandelate, benzoate, cinnamate, methanesulfonate, ethanesulfonate, picrate and the like, and include acids related to the pharmaceutically acceptable salts listed in Berge, S. M., et al., "Pharmaceutical Salts" 66(1) J. Pharm. Sci. 1-19 (1977).

Methods of Use

A compound of Formula (I) or pharmaceutically acceptable salt thereof, a pharmaceutical composition comprising a compound of Formula (I), a pharmaceutically acceptable salt of a compound of Formula (I), or a pharmaceutical composition comprising a pharmaceutically acceptable salt of a compound of Formula (I), may be used for the treatment of a disease, disorder, or condition. In some embodiments, the disease, disorder or condition is a cancer such as, but not limited to, colon cancer, hematological malignancies and cutaneous T-cell lymphomas.

In one embodiment, a method of treatment is provided comprising administering a compound of Formula (I) or a pharmaceutically acceptable salt to a subject, e.g. a human. In another embodiment, a method of treatment is provided comprising administering at least 0.1 milligrams/day of a compound of Formula (I) or a pharmaceutically acceptable salt thereof to a human. In another embodiment, a method of treatment of any of the diseases, disorders, or conditions described above is provided, comprising administering an effective amount of a compound of Formula (I) or a pharmaceutically acceptable salt thereof to a subject (e.g., a human). As used herein, the term "effective amount" is an amount sufficient to induce the desired therapeutic effect in a subject to whom the compound is administered.

In another embodiment, a compound of Formula (I) or a pharmaceutically acceptable salt thereof is provided for use in medicine. In another embodiment, a compound of Formula (I) or a pharmaceutically acceptable salt thereof is provided for use in the treatment of at least one disease, disorder, or condition selected from those described above.

In each of the methods or uses described above, a compound of Formula (I) or a pharmaceutically acceptable salt thereof may be administered to a subject as part of a pharmaceutically formulation, as described above.

Examples of compounds of Formula (I) or pharmaceutically acceptable salts thereof having potentially useful biological activity are listed in Table 1. The ability of compounds Formula (I) or pharmaceutically acceptable salts thereof to inhibit HDAC was established with the representative compounds of Formula (I) listed in Table 1 using the assays described below.

Inhibition Assay

Key enzyme kinetic parameters for one class I HDAC (HDAC8) and one class IIa HDAC (HDAC4) were determined using commercially available human recombinant HDAC enzymes (BPS Bioscience, San Diego, Calif.) and fluorogenic HDAC assay kits (BPS Bioscience). Kinetic parameters were determined by performing HDAC activity assays at varied concentrations of the HDAC substrate according to the manufacturer's protocol. Assay data were analyzed via non-linear regression (GraphPad Software, Inc., CA). Inhibition assays were used to determine the half maximal inhibitory concentration, $IC_{50}$, for tropolone analogs in HDAC8 and HDAC6. The potent hydroxamic acid HDAC inhibitor, Trichostatin A (TSA), provided in the assay kit, served as a control for the assays. $IC_{50}$ values for the tropolone analogs were converted to inhibition constants, $K_i$, for each of the inhibitors using the $K_M$ value in accordance with the techniques previously described by Cheng and Prusoff. Assay results for various example compounds are shown in Table 1.

Cell-Based Assay

All cell lines were purchased from ATCC (Manassas, Va.). Jurkat cells were cultured in RPMI 1640 (ATCC) supplemented with 10% fetal bovine serum (FBS; Atlanta Biologicals, Lawrenceville, Ga.). HuT-78 cells were cultured in IMDM (ATCC) supplemented with 20% FBS (Atlanta Biologicals). HT-29 and HCT116 were cultured in McCoy's media (Life Technologies, Carlsbad Calif.) supplemented with 10% FBS (Atlanta Biologicals), 1% non-essential amino acids (Mediatech Inc., Manassas, Va.) and 1% penicillin/streptomycin (Mediatech Inc).

Confluent Jurkat and HuT-78 cells were seeded in triplicate at a density of $5 \times 10^4$ cells/well whereas HT-29 and HCT116 cells were seeded in triplicate at a density of $5 \times 10^3$ cells/well in 96-well plates. Cells were treated at varying concentrations (1 µM-100 µM) of either a tropolone analog or SAHA. DMSO served as a vehicle control. After a 72-h exposure, cytotoxicity was evaluated using the Cell Titer 96 Aqueous One kit (Promega, Madison, Wis.) according to the instructions of the manufacturer. Formazan content was determined by measuring the absorbance at 490 nm on an Infinite M200 microplate reader (Tecan Group Ltd., Switzerland) and analyzed via non-linear regression analysis (GraphPad Software, Inc.). Assay results for various example compounds are shown in Table 1.

While the invention has been described and illustrated with reference to certain embodiments thereof, those skilled in the art will appreciate that various changes, modifications and substitutions can be made therein without departing from the spirit and scope of the invention. For example, effective dosages other than the dosages as set forth herein may be applicable as a consequence of variations in the responsiveness of the subject being treated. Likewise, the specific pharmacological responses observed may vary according to and depending on the particular active compound selected or whether there are present pharmaceutical carriers, as well as the type of formulation and mode of administration employed, and such expected variations or differences in the results are contemplated in accordance with the objects and practices of the present invention. Moreover, all compounds that are recited in the written description are contemplated as possibilities for any of the recited methods, processes, compositions, and/or compounds as appear in the written description and the appended claims.

The invention claimed is:

1. A pharmaceutical formulation comprising a compound of Formula (I) or a pharmaceutically acceptable salt thereof:

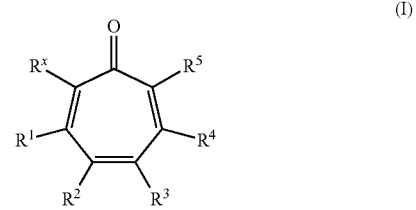

wherein:
$R^x$ is hydrogen, hydroxyl, or amino;
$R^1$, $R^2$, and $R^3$ are hydrogen;
wherein when $R^x$ is hydrogen, then $R^4$ and $R^5$ are independently hydrogen, $C_4$-$C_6$ alkyl, $C_3$-$C_6$ cycloalkyl, naphthyl, or alkoxy substituted phenyl, wherein when the alkoxy substitution is methoxy, then the phenyl includes at least two substitutions;
wherein when $R^x$ is hydroxyl, then $R^4$ and $R^5$ are independently hydrogen, $C_4$-$C_6$ alkyl, $C_3$-$C_6$ cycloalkyl, naphthyl, or alkoxy substituted phenyl;
wherein when $R^x$ is amino, then $R^4$ and $R^5$ are independently hydrogen, $C_1$-$C_6$ alkyl, $C_3$-$C_6$ cycloalkyl, naphthyl, phenyl, or alkoxy substituted phenyl;
provided that $R^4$ and $R^5$ are not both hydrogen;
and a pharmaceutically acceptable carrier.

2. The pharmaceutical formulation of claim 1, wherein $R^4$ is hydrogen.

3. The pharmaceutical formulation of claim 1, wherein $R^4$ is tert butyl, sec butyl, or cyclopentyl.

4. The pharmaceutical formulation of claim 1, wherein $R^4$ is methoxyphenyl, dimethoxyphenyl, or trimethoxyphenyl.

5. The pharmaceutical formulation of claim 1, wherein $R^5$ is hydrogen.

6. The pharmaceutical formulation of claim 1, wherein $R^5$ is tert butyl, sec butyl, or cyclopentyl.

7. The pharmaceutical formulation of claim 1, wherein $R^5$ is methoxyphenyl, dimethoxyphenyl, or trimethoxyphenyl.

8. A method of inhibiting histone deacetylase (HDAC) activity, comprising contacting an HDAC isoform with a compound of Formula (I) or a pharmaceutically acceptable salt thereof:

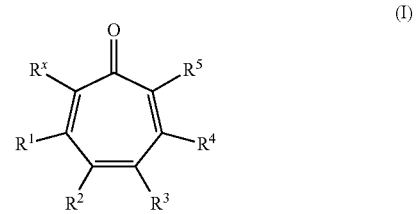

wherein:
$R^x$ is hydrogen, hydroxyl, or amino;
$R^1$, $R^2$, and $R^3$ are hydrogen;

$R^4$ and $R^5$ are independently hydrogen, $C_1$-$C_6$ alkyl, $C_3$-$C_{10}$ cycloalkyl, or aryl, wherein the aryl is unsubstituted or substituted one, two, or three times with $C_1$-$C_6$ alkoxy; and provided that $R^4$ and $R^5$ are not both hydrogen.

9. The method of claim 8, wherein the HDAC isoform is HDAC-2.

10. The method of claim 8, wherein the HDAC isoform is HDAC-4.

11. The method of claim 8, wherein the HDAC isoform is HDAC-8.

12. The method of claim 8, wherein the HDAC activity is inhibited in a subject.

13. The method of claim 12, wherein the HDAC is HDAC-2.

14. The method of claim 12, wherein the HDAC is HDAC-4.

15. The method of claim 12, wherein the HDAC is HDAC-8.

16. A method of treating a disease in a subject, comprising administering to a subject an amount of a compound of Formula (I) or a pharmaceutically acceptable salt thereof:

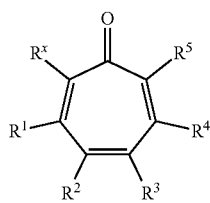

(I)

wherein:
$R^x$ is hydrogen, hydroxyl, or amino;
$R^1$, $R^2$, and $R^3$ are hydrogen;
$R^4$ and $R^5$ are independently hydrogen, $C_1$-$C_6$ alkyl, $C_3$-$C_{10}$ cycloalkyl, or aryl, wherein the aryl is unsubstituted or substituted one, two, or three times with $C_1$-$C_6$ alkoxy;
provided that $R^4$ and $R^5$ are not both hydrogen.

17. The method of claim 16, wherein the amount is an effective amount.

18. The method of claim 16, wherein the disease is cancer.

19. The method of claim 18, wherein the cancer is colon cancer.

20. The method of claim 18, wherein the cancer is cutaneous T-cell lymphoma.

21. The pharmaceutical formulation of claim 1, wherein the pharmaceutical formulation is a solid pharmaceutical formulation.

22. The pharmaceutical formulation of claim 1, wherein the pharmaceutical formulation is a liquid pharmaceutical formulation and the pharmaceutically acceptable carrier is an aqueous medium.

23. The method of claim 8, wherein $R^4$ and $R^5$ are independently hydrogen, $C_4$-$C_6$ alkyl, $C_3$-$C_6$ cycloalkyl, naphthyl, phenyl, or substituted phenyl.

24. The method of claim 8, wherein $R^4$ and $R^5$ are independently hydrogen, tert butyl, sec butyl, cyclopentyl, methoxyphenyl, dimethoxyphenyl, or trimethoxyphenyl.

25. The method of claim 12, wherein $R^4$ and $R^5$ are independently hydrogen, $C_4$-$C_6$ alkyl, $C_3$-$C_6$ cycloalkyl, naphthyl, phenyl, or substituted phenyl.

26. The method of claim 12, wherein $R^4$ and $R^5$ are independently hydrogen, tert butyl, sec butyl, cyclopentyl, methoxyphenyl, dimethoxyphenyl, or trimethoxyphenyl.

27. The method of claim 16, wherein $R^4$ and $R^5$ are independently hydrogen, $C_4$-$C_6$ alkyl, $C_3$-$C_6$ cycloalkyl, naphthyl, phenyl, or substituted phenyl.

28. The method of claim 16, wherein $R^4$ and $R^5$ are independently hydrogen, tert butyl, sec butyl, cyclopentyl, methoxyphenyl, dimethoxyphenyl, or trimethoxyphenyl.

* * * * *